(12) United States Patent
Gueret

(10) Patent No.: US 6,730,317 B2
(45) Date of Patent: *May 4, 2004

(54) PATCH, A KIT CONSTITUTED BY A PATCH AND A RECEPTACLE AND A METHOD

(75) Inventor: Jean-Louis Gueret, Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/418,825

(22) Filed: Oct. 15, 1999

(65) Prior Publication Data

US 2002/0086043 A1 Jul. 4, 2002

(30) Foreign Application Priority Data

Oct. 20, 1998 (FR) .............................. 98 13129

(51) Int. Cl.[7] .................. A61F 13/00; A61K 9/70; A61L 15/16
(52) U.S. Cl. .................. 424/443; 424/445; 424/446; 424/447; 424/448; 424/449; 424/484; 424/486; 424/487; 424/489
(58) Field of Search .............. 424/401, 402, 424/448, 447, 443, 445, 446, 449, 484, 486, 487, 489

(56) References Cited

U.S. PATENT DOCUMENTS

| 4,356,969 | A | * | 11/1982 | Obermayer et al. ........... 239/6 |
| 4,592,753 | A | * | 6/1986 | Panoz ........................ 604/897 |
| 4,743,231 | A | * | 5/1988 | Kay et al. .................... 604/180 |
| 5,028,435 | A | * | 7/1991 | Katz et al. .................. 424/484 |
| 5,156,846 | A | * | 10/1992 | Petersen et al. ............ 424/443 |
| 5,176,915 | A | * | 1/1993 | Hoffmann ................... 424/445 |
| 2003/0044599 | A1 | | 3/2003 | Sugii et al. |

FOREIGN PATENT DOCUMENTS

| EP | 0 674 913 A2 | 10/1995 |
| EP | 0 764 441 A1 | 3/1997 |
| JP | 10-287530 | 10/1998 |
| WO | WO 99/36032 | * 7/1999 |

* cited by examiner

Primary Examiner—Thurman K. Page
Assistant Examiner—Liliana Di Nola-Baron
(74) Attorney, Agent, or Firm—Oliff & Berridge, PLC

(57) ABSTRACT

A patch comprising a matrix having adhesive properties in the dry state and containing at least one active substance, said matrix being attached via one face to a backing and being for application via its other face to the skin. Said backing is selected in such a manner as to be capable of containing a predetermined liquid suitable for dissolving at least in part the active substance(s) contained in the matrix, and said matrix is permeable to the liquid.

28 Claims, 1 Drawing Sheet

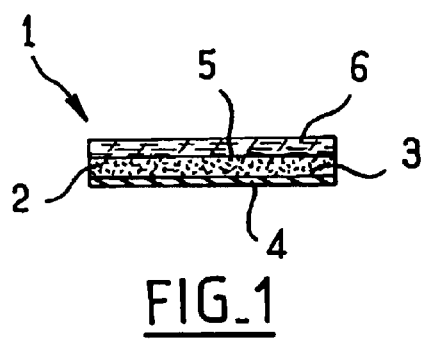
FIG.1
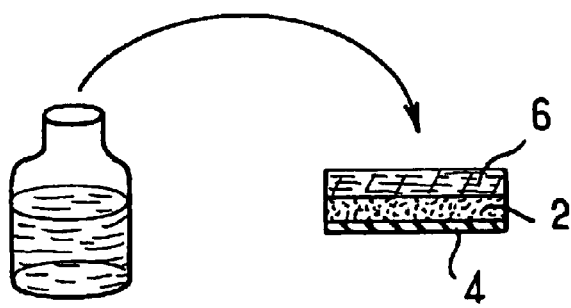
FIG.2
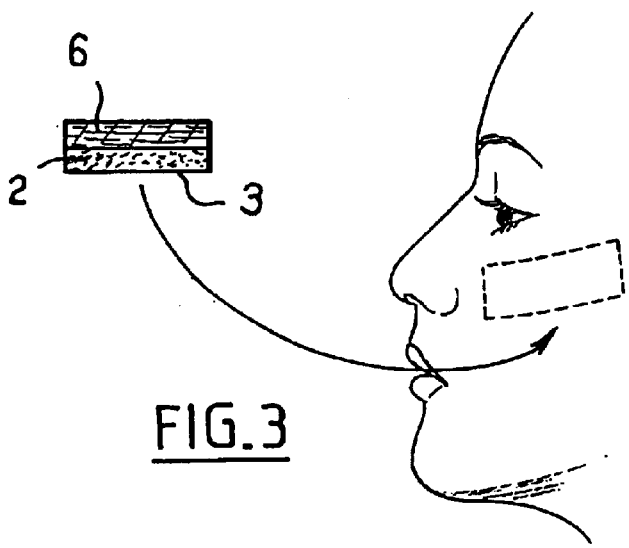
FIG.3
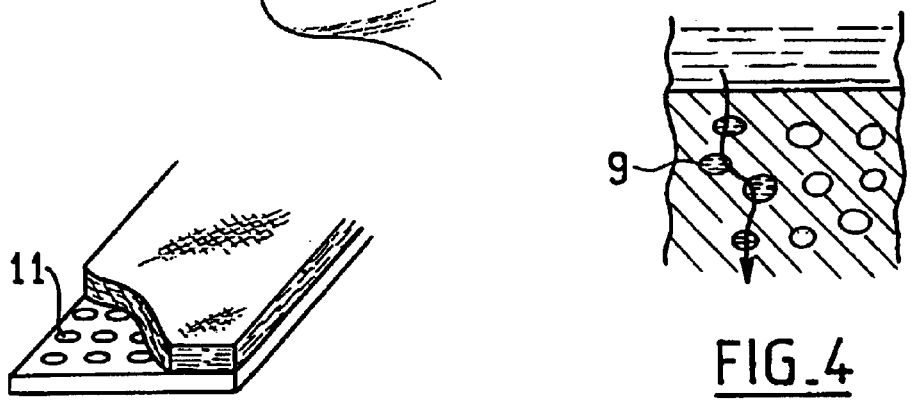
FIG.4
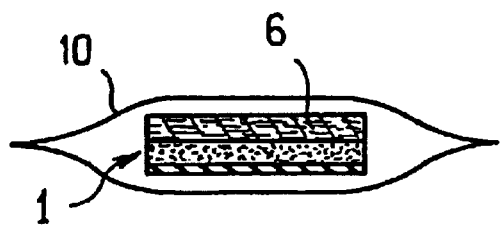
FIG.5
FIG.6

PATCH, A KIT CONSTITUTED BY A PATCH AND A RECEPTACLE AND A METHOD

The present invention relates to a patch for application to the skin to perform some determined treatment, for example a cosmetic treatment with active substances being released to perform some given action on the epidermis.

BACKGROUND OF THE INVENTION

Numerous patches of that type are known, and in general they present a multilayer structure comprising an adhesive matrix based on one or more polymers designed on one face to come directly into contact with the skin and on the other face to be attached to a backing.

The invention relates more particularly to patches in which the matrix presents adhesive properties when in the dry state.

In such patches, the matrix advantageously contains one or more active substances to be released on the epidermis to exercise a given effect, for example a hydrating or regenerating action.

Such active substances can be released by wetting the skin before applying the patch.

In a variant, the water for putting into solution the active substances contained in particular at the surface of the matrix can come from the region of the skin that is situated beneath the patch, in which case it is preferable to use a backing that is occlusive so as to favor local transpiration.

Known patches do not give entire satisfaction.

In particular, the quantity of water deposited on the skin prior to application of the patch can turn out to be insufficient to put the active substances contained in the matrix into solution as described.

In addition, an occlusive backing can be rather uncomfortable in use, providing a heating effect rather than a cooling or freshening effect.

Consequently, there exists a need to further improve the conditions under which one or more active substances are applied to the skin by means of a patch.

OBJECTS AND SUMMARY OF THE INVENTION

The present invention provides a novel patch of the type comprising a matrix having adhesive properties in the dry state and containing at least one active substance, said matrix being attached via one face to a backing and being for application via its other face to the skin, wherein said backing is selected in such a manner as to be capable of containing a predetermined liquid suitable for dissolving at least in part the active substance(s) contained in the matrix, and wherein said matrix is permeable to the liquid.

Thus, by means of the invention, the liquid (which can be water or any other solvent) can diffuse towards the skin through the matrix from the backing which then constitutes a kind of reservoir, and this presents multiple advantages.

Firstly, as it diffuses through the matrix, the liquid causes the above-mentioned active substance(s) to pass into solution, thereby releasing the substance(s) from the matrix.

The matrix can act like a "wick" tending to absorb the liquid impregnating the backing by capillarity, and it can also act like a "filter" by retaining particles while allowing dissolved active substances to pass through.

In addition, in particular when the liquid is water and the patch is applied on wet skin, the water-impregnated backing serves to retard drying of the interface with the skin and thus behaves as a kind of occlusive backing, while avoiding the drawbacks specific to using an occlusive backing, in particular the drawbacks concerning user comfort.

Fluid flow can also be established between the interface with the skin and the liquid-impregnated backing, which is favorable for the breathing of the skin and for renewing the active substances that come into contact with the skin and/or for eliminating to the backing any impurities or toxins that can be released at the interface with the skin.

Finally, the thermal inertia of the soaked backing and the evaporation of the liquid from its surface gives the user a feeling of coolness or freshness which further increases user comfort.

In a preferred implementation of the invention, the matrix comprises one or more polymers which may be elastomers.

The liquid used for impregnating the backing can be water or an aqueous or alcohol solution, in which case the matrix preferably includes at least one hydrophobic polymer.

The backing is advantageously constituted by a porous matrix, e.g. a non-woven cloth.

The active substance(s) contained in the matrix can be cosmetically active compounds, preferably hydrosoluble compounds, and can be dispersed in the matrix in particulate form.

The cosmetically active compound(s) is selected, for example, from: emollients, moisturizers, healing agents, regenerating agents, anti-wrinkle agents, tightening agents, anesthetics, sun screens, soothing agents, self-tanning agents, brightening agents, concealers, grease reducers, and mixtures thereof.

In a preferred implementation of the invention, the matrix also contains in dispersion a filler of particles of at least one liquid-absorbing compound, e.g. a water-absorbing hydrophilic compound when the liquid used is water or an aqueous solution or an alcohol solution.

The water-absorbing compound is then selected, for example, from the following list: superabsorbent crosslinked polyacrylates having a large swelling factor in water, polyvinyl alcohol, carboxyvinyl polymers, semi-synthetic derivatives of cellulose, starches, biogums, biosaccharides, scleroglucanes, casein, photocolloids such as alginates, gelatin, cotton fibers, gellanes, xanthanes, laponite, silicas, or mixtures thereof. By way of example, the liquid-absorbing compound filler is at a concentration lying in the range 0.2% to 50% by weight, preferably in the range 1% to 20%, more preferably in the range 1% to 10%, relative to the total weight of the matrix.

Preferably, the content in the matrix of liquid-absorbing compound(s) is selected so that the quantity of liquid that can be absorbed by said compound(s) is greater than or equal to the quantity of liquid required for dissolving the active substance(s) contained in the matrix.

The matrix may have gaps, e.g. microperforations for making the matrix permeable to the liquid in which the backing is soaked and/or for favoring the exchange of gas and/or liquid between the backing and the interface with the skin.

The matrix can be deposited on the backing in a grid pattern or the like.

The matrix can contain at least one active substance capable of reacting chemically with the liquid used.

In a particular embodiment, the patch is contained in a hermetically sealed package and the backing is already impregnated by a liquid.

The invention also provides a kit constituted by a patch as defined above together with a receptacle containing a liquid for impregnating the backing attached to the matrix.

The liquid can include at least one active substance for exercising a predetermined effect on the skin, which effect can be cosmetic or otherwise, for example an anesthetic.

The invention also provides a method comprising the steps consisting in:

supplying a patch as defined above; and impregnating the backing with a determined liquid before or after application to the skin.

In a particular implementation of the method, the skin is wetted prior to the patch being applied thereto.

The quantity of water soaking the backing per unit area of the backing is preferably greater than the quantity of water deposited on the skin per unit area.

The patch is left on the skin, for example, for a length of time lying in the range 5 minutes (min) to 60 min.

BRIEF DESCRIPTION OF THE DRAWING

Other characteristics and advantages of the present invention will appear on reading the following detailed description of non-limiting embodiments of the invention, and on examining the accompanying drawing, in which:

FIG. 1 is a diagrammatic section view of a patch constituting a first embodiment of the invention;

FIGS. 2 and 3 show how the patch of FIG. 1 is used;

FIG. 4 is a diagrammatic view showing one way in which the liquid soaking the backing can propagate through the matrix;

FIG. 5 is a diagrammatic perspective view of a patch constituting a variant embodiment of the invention; and FIG. 6 is a diagrammatic section view of a patch contained in a hermetically sealed package.

MORE DETAILED DESCRIPTION

The patch 1 shown in FIG. 1 comprises a matrix 2 based on a hydrophobic polymer, which matrix is coated on one face 3 in a removable protective film 4 and has its other face 5 attached to a porous backing 6 which is constituted in the embodiment described by a non-woven cloth based on cellulose fibers.

In this case, the matrix 2 is made of polyacrylic adhesive and it presents adhesive properties when in the dry state.

The matrix 2 is advantageously colored so as to enable the user to see any impurities that might be adhering to the surface of the patch after it is removed.

Other hydrophobic adhesive materials suitable for use in general terms in the context of the present invention include silicone or polyvinyl adhesives, polyurethanes, latex elastomers, and EPDM elastomers, said list being given in non-limiting manner.

In the example described, the matrix 2 contains a filler of particles 9 of a water-absorbing hydrophilic compound and it also contains cosmetically active compounds that are soluble in the liquid used for impregnating the backing.

The thickness of the matrix is readily chosen as a function of the nature of the treatment for which the patch is intended, the nature of the filler, and the nature of the cosmetically active compound(s) contained therein.

The thickness of the matrix 2 in general lies in the range 2 $\mu$m to 1.5 mm, and preferably lies in the range 5 $\mu$m to 500 $\mu$m. In the example described it is equal to 200 $\mu$m.

The particles 9 are dispersed in the polymer constituting the matrix 2, as shown very diagrammatically in FIG. 4.

The average size of the particles 9 can lie in the range 5 $\mu$m to 70 $\mu$m, for example, and the particles can project from the outside face 3 of the matrix 2 that is to be applied to the skin.

The particles 9 present at the surface of the matrix 2 are then coated in a very fine layer of the polymer constituting the matrix.

In the example described, the water-absorbing hydrophilic material used is a hydro-absorbent polyacrylate sold by ATO under the name AQUAKEEP, and its concentration in the matrix 2 is about 10% by weight.

The matrix 2 in the example described contains the following cosmetically active compounds, each generally being present at a concentration by weight of less than 6%: ascorbic acid (4%); menthol (0.05%); lavender essence (1%); polyamide powder (3%); citric acid (1%); allantoin (1%).

The adhesive power of the patch on dry skin is about 500 g/cm$^2$ (the force to be exerted perpendicularly to the plane of the surface of the adhesive to unstick it).

In the example described, the thickness of the backing 6 is 2 mm, and said thickness is generally preferably less than 3 mm so as to avoid excessively stiffening the patch and so as to avoid projecting too far from the skin.

To use the patch of FIG. 1, the backing 6 is wetted so as to be completely soaked in water or in an aqueous solution such as a lotion, as shown in FIG. 2, and then the protective sheet 4 is removed and the patch is applied via the outside face 3 of the matrix 2 onto the zone that is to be treated, as shown in FIG. 3.

In the example described, the skin is initially wetted, however in a variant, application can be performed on dry skin, depending on the kind of treatment that is to be performed.

The matrix 2 is made permeable to the liquid impregnating the backing 6 because of the presence of the particles 9 of the water-absorbing hydrophilic compound, with water passing through the matrix 2 by being absorbed by said particles 9, as represented highly diagrammatically by FIG. 4.

The particles 9 which are to be found in the vicinity of the interface with the skin, by becoming waterlogged, can constitute a gelled intermediate layer between the matrix 2 and the skin, in which layer the cosmetically active compounds are dissolved, thereby releasing them in contact with the epidermis.

By releasing the cosmetically active compounds by dissolving them in the liquid deposited on the skin and impregnating the backing 6, it is possible to include cosmetically active compounds in the matrix 2 which would be impossible to conserve over a long period in the same solution.

The backing 6 delays drying out of the patch at the interface with the skin, thus favoring prolonged action of the cosmetically active compounds in the skin and good diffusion thereof into the epidermis, where appropriate.

The water-impregnated backing 6 also gives the user a feeling of coolness or freshness.

Finally, impurities or toxins present at the surface of the skin can be dissolved at the surface of the matrix and can diffuse into the matrix towards the impregnated backing 6, under the effect of concentration gradients.

Thus, the presence of the water-soaked backing 6 can favor cleaning of the skin.

In the example described, when the patch is removed after about 30 min, it can be seen that the treated zone has become paler because of the presence of ascorbic acid and of citric acid. The skin also becomes more flexible and softer.

As shown in FIG. 5, it is also possible to make gaps in the matrix 2 without going beyond the ambit of the present invention.

The gaps can be constituted by microperforations 11 or they can be obtained by depositing the matrix 2 on the backing 6 in the form of a grid of smaller or larger mesh.

FIG. 6 shows a hermetically sealed sachet 10 containing the patch 1 of FIG. 1, the backing 6 of the patch is already impregnated by the liquid, thereby avoiding any need for the user to wet the backing 6, and also making it possible to use a liquid other than water.

Naturally, the invention is not limited to the embodiments described above.

In particular, it is possible to use a liquid containing one or more active substances for exercising some determined effect on the skin, for example an anesthetic to make the skin locally insensitive.

The backing can be a non-woven cloth based on cellulose fibers as in the example described, or in a variant it can be constituted by or can include a felt, a foam, or a material which is capable because of its chemical structure of containing the liquid used, for example a water-swelling material.

What is claimed is:

1. A patch comprising:
   a matrix having adhesive properties in a dry state and containing at least one active substance;
   said matrix being attached via one face to a porous backing and being for application via its other face to the skin;
   wherein said backing is capable of containing a liquid suitable for dissolving, at least in part, said at least one active substance;
   wherein said matrix is permeable to the liquid; and
   wherein said at least one active substance is not suitable for migrating through the matrix, toward the other face for application to the skin, without addition of said liquid to the patch.

2. A patch according to claim 1, wherein the matrix comprises one or more polymers.

3. A patch according to claim 2, wherein said liquid is water or an aqueous or alcohol solution, and wherein said matrix comprises at least one hydrophobic polymer.

4. A patch according to claim 1, wherein said backing is constituted by a non-woven cloth.

5. A patch according to claim 1, wherein the matrix contains at least one active substance which is a cosmetically active compound.

6. A patch according to claim 5, wherein the cosmetically active compound is selected from: emollients, moisturizers, healing agents, regenerating agents, anti-wrinkle agents, tightening agents, anesthetics, sun screens, soothing agents, self-tanning agents, brightening agents, concealers, grease reducers, and mixtures thereof.

7. A patch according to claim 1, wherein the matrix contains in dispersion a filler of particles of at least one compound that absorbs the liquid contained in the backing.

8. A patch according to claim 7, wherein the concentration in the matrix of the absorbing compound(s) is selected in such a manner that the quantity of liquid that can be absorbed thereby is greater than or equal to the quantity of liquid required for dissolving the active substance(s) contained in the matrix.

9. A patch according to claim 7, wherein the absorbing compound(s) is/are selected from the following list: superabsorbent cross-linked polyacrylates having a large swelling factor in water, polyvinyl alcohol, carboxyvinyl polymers, semi-synthetic derivatives of cellulose, starches, biogums, biosaccharides, scleroglucanes, casein, photocolloids such as alginates, gelatin, cotton fibers, gellanes, xanthanes, laponite, silicas, or mixtures thereof.

10. A patch according to claim 7, wherein said filler is at a concentration lying in the range 0.2% to 50% by weight, preferably in the range 1% to 20%, more preferably in the range 1% to 10% relative to the total weight of the matrix.

11. A patch according to claim 1, wherein said matrix has gaps.

12. A patch according to claim 11, wherein said matrix has microperforations.

13. A patch according to claim 1, wherein said matrix is deposited on said backing in a grid pattern or the like.

14. A patch according to claim 1, wherein said matrix contains at least one active substance capable of reacting chemically with said liquid.

15. A patch according to claim 1, contained in a hermetically sealed package and wherein said backing is already impregnated by a liquid.

16. A kit constituted by a patch as defined in claim 1, and a receptacle containing a liquid for impregnating said backing.

17. A kit according to claim 16, wherein the liquid includes at least one active substance for exercising a predetermined effect on the skin.

18. A method comprising:
    supplying a patch as defined in claim 1; and
    impregnating said patch with said liquid before or after applying the patch to the skin.

19. A method according to claim 18, wherein prior to application of the patch on the skin, the skin is wetted.

20. A method according to claim 19, said liquid being water, wherein the quantity of water per unit area of the backing that soaks up the water is greater than the quantity of water deposited on the skin, per unit area.

21. A method according to claim 18, wherein the patch is left on the skin for a length of time lying in the range 5 min to 60 min.

22. A kit according to claim 17, wherein said active substance for exercising a predetermined effect on the skin is an anesthetic.

23. A patch comprising:
    a matrix having adhesive properties in a dry state and containing at least one active substance present in particulate form;
    said matrix being attached via one face to a porous backing and being for application via its other face to the skin;
    wherein said backing is capable of containing a liquid suitable for dissolving, at least in part, said at least one active substance;
    wherein said matrix is permeable to the liquid; and
    wherein said at least one active substance is not suitable for migrating through the matrix, toward the other face for application to the skin, in the absence of said liquid added to the patch.

24. The patch according to claim 23, wherein said at least one active substance is in a solid state.

25. A patch comprising:
    a matrix having adhesive properties in a dry state and containing at least one active substance;

said matrix being attached via one face to a porous backing and being for application via its other face to the skin;

wherein said backing is capable of containing a liquid suitable for dissolving, at least in part, said at least one active substance;

wherein said matrix is permeable to the liquid, said backing and said matrix being free of said liquid until use; and wherein said at least one active substance is not suitable for migrating through the matrix, toward the other face for application to the skin, in the absence of said liquid.

26. The patch of claim 23, wherein said at least one active substance is not suitable for migrating through the matrix, toward the other face for application to the skin, in the absence of said liquid added to said backing of said patch.

27. The patch of claim 1, wherein said at least one active substance is not suitable for migrating through said matrix, toward the other face for application to the skin, without addition of said liquid to said backing of said patch.

28. The method of claim 18, wherein impregnating said patch with said liquid comprises impregnating said backing.

* * * * *